(12) United States Patent
Pollner et al.

(10) Patent No.: US 8,097,409 B2
(45) Date of Patent: Jan. 17, 2012

(54) KITS FOR DETECTING GROUP B STREPTOCOCCI

(75) Inventors: Reinhold B. Pollner, San Diego, CA (US); Edgar J. Kamantigue, San Diego, CA (US)

(73) Assignee: Gen-Probe Incorporated, San Diego, CA (US)

( * ) Notice: Subject to any disclaimer, the term of this patent is extended or adjusted under 35 U.S.C. 154(b) by 242 days.

(21) Appl. No.: 12/391,123

(22) Filed: Feb. 23, 2009

(65) Prior Publication Data

US 2009/0176241 A1 Jul. 9, 2009

Related U.S. Application Data

(62) Division of application No. 11/349,615, filed on Feb. 7, 2006, now abandoned.

(60) Provisional application No. 60/650,501, filed on Feb. 7, 2005.

(51) Int. Cl.
*C12Q 1/68* (2006.01)
*C12P 19/34* (2006.01)
*C07H 21/04* (2006.01)
*C07H 21/00* (2006.01)

(52) U.S. Cl. ....... 435/6; 435/91.1; 435/91.2; 435/91.21; 536/24.1; 536/24.3; 536/24.32; 536/24.33; 536/25.3; 536/25.32

(58) Field of Classification Search .................. None
See application file for complete search history.

(56) References Cited

U.S. PATENT DOCUMENTS

| | | |
|---|---|---|
| 4,581,333 A | 4/1986 | Kourilsky et al. |
| 4,868,105 A | 9/1989 | Urdea et al. |
| 4,965,188 A | 10/1990 | Mullis et al. |
| 5,118,801 A | 6/1992 | Lizardi et al. |
| 5,124,246 A | 6/1992 | Urdea et al. |
| 5,130,238 A | 7/1992 | Malek et al. |
| 5,283,174 A | 2/1994 | Arnold, Jr. et al. |
| 5,312,728 A | 5/1994 | Lizardi et al. |
| 5,399,491 A | 3/1995 | Kaclan et al. |
| 5,401,631 A | 3/1995 | Lane et al. |
| 5,437,990 A | 8/1995 | Burg et al. |
| 5,455,166 A | 10/1995 | Walker |
| 5,472,840 A | 12/1995 | Stefano |
| 5,547,842 A | 8/1996 | Hogan et al. |
| 5,554,516 A | 9/1996 | Kacian et al. |
| 5,585,481 A | 12/1996 | Arnold, Jr. et al. |
| 5,591,578 A | 1/1997 | Meade et al. |
| 5,639,604 A | 6/1997 | Arnold, Jr. et al. |
| 5,656,207 A | 8/1997 | Woodhead et al. |
| 5,658,737 A | 8/1997 | Nelson et al. |
| 5,770,369 A | 6/1998 | Meade et al. |
| 5,786,183 A | 7/1998 | Ryder et al. |
| 5,840,488 A | 11/1998 | Hogan |
| 5,925,517 A | 7/1999 | Tyagi et al. |
| 6,074,826 A | 6/2000 | Hogan et al. |
| 6,361,945 B1 | 3/2002 | Becker et al. |
| 6,559,294 B1 | 5/2003 | Griffais et al. |
| 6,593,114 B1 | 7/2003 | Kunsch et al. |
| 6,737,248 B2 | 5/2004 | Kunsch et al. |
| 6,783,961 B1 | 8/2004 | Edwards et al. |
| 2004/0009574 A1 | 1/2004 | Dattagupta et al. |

FOREIGN PATENT DOCUMENTS

| | | |
|---|---|---|
| EP | 0525882 A1 | 2/1993 |
| WO | 8801302 A1 | 2/1988 |
| WO | 8810315 A1 | 12/1988 |
| WO | 9313121 A1 | 7/1993 |
| WO | 9532305 A1 | 11/1995 |
| WO | 9857158 A1 | 12/1998 |
| WO | 0234771 A2 | 5/2002 |
| WO | 02092818 A2 | 11/2002 |
| WO | 03025216 A1 | 3/2003 |
| WO | 03080870 A1 | 10/2003 |
| WO | 2004029299 A2 | 4/2004 |

OTHER PUBLICATIONS

Hill, Craig. Gen-Probe Transcription-Mediated Amplification: Systems and Principles. 1996, retrieved from http://www.gen-probe.com/pdfs/tma_whiteppr.pdf.*

Tan et al., "Molecular Beacons: A Novel DNA Probe for Nucleic Acid and Protein Studies," Chem. Eur. J., 2000, pp. 1107-1111, vol. 6:No. 7, WILEY-VCH Verlag GmbH & Co. KGaA, Weinheim Gemany.

Sequence alignment for SEQ ID No. 3. pp. 3: acession # ABN72583 Geneseq database Jul. 2, 2002.

Supplement to Telford et al. WO200234771A2, p. 3024-3057 and p. 1370-1371 May 2, 2002.

EPO Rule 71(3) EPC Communication, European Patent Application No. 06734549.6, Jun. 23, 2010.

Kircher et al., "Comparison of a Modified DNA Hybridization Assay with Standard Culture Enrichment for Detecting Group B *Streptococci* in Obstetric Patients," J. Clinical Microbiology, 1996, pp. 342-344, vol. 34(2), American Society for Microbiology, Washington, D.C.

Tyagi et al., "Molecular Beacons: Probes that Fluoresce upon Hybridization," Nature Biotechnology, Mar. 1, 1996, pp. 303-308, vol. 14, Nature Publishing Group, USA.

Ke et al., "Development of Conventional and Real-Time PCR Assays for the Rapid Detection of Group B *Streptococci*," Clinical Chemistry, 2000, pp. 324-331, vol. 46(3), American Association for Clinical Chemistry, Washington, D.C.

Adams et al., "The Structure of the Nucleic Acids", The Biochemistry of the Nucleic Acids, 11th ed., Chpt. 2, 1992, Sect. 2.1-2.7.4, pp. 5-39, Chapman and Hall, London, UK.

Lizardi et al., "Exponential Amplification of Recombinant—RNA Hybridization Probes", BioTechnology, 1988, 6:1197-1202, Nature Publications Group, Macmillan Pub. Ltd., GB.

Sambrook et al., Molecular Cloning: A Laboratory Manual, 1st ed. (Cold Spring Harbor Laboratory Press, Cold Spring Harbor, NY, 1989) at §§ 1.90-1.91, 7.37-7.57, 9.47-9.51 and 11.47-11.57, particularly at §§ 9.50-9.51, 11.12-11.13, 11.45-11.47 and 11.55-11.57.

Sambrook et al., Molecular Cloning: A Laboratory Manual, 2nd ed. (Cold Spring Harbor Laboratory Press, Cold Spring Harbor, NY, 1989), Chapter 10.

* cited by examiner

*Primary Examiner* — Oluwatosin Ogunbiyi

(74) *Attorney, Agent, or Firm* — Charles B. Cappellari; Yan Leychkis

(57) ABSTRACT

Compositions, methods and kits for detecting Group B streptococci. Particularly described are oligonucleotides that are useful as amplification primers and hybridization probes for detecting very low levels of Group B streptococci nucleic acids.

14 Claims, 1 Drawing Sheet

KITS FOR DETECTING GROUP B STREPTOCOCCI

RELATED APPLICATIONS

This application is a divisional of U.S. application Ser. No. 11/349,615, filed Feb. 7, 2006, now abandoned, which claims the benefit of U.S. Provisional Application No. 60/650,501, filed Feb. 7, 2005.

FIELD OF THE INVENTION

The present invention relates to the field of biotechnology. More specifically, the invention relates to diagnostic assays for detecting the nucleic acids of Group B streptococci (GBS).

BACKGROUND OF THE INVENTION

*Streptococcus agalactiae*, more commonly known as Group B *Streptococcus*, is one of the leading causes of septicemia and meningitis in newborns. The incidence of Group B disease is estimated to be 2-5 infants per 1000 live births. The early onset form of this disease occurs during the first week of life and has a mortality rate greater than 50%. When the onset occurs after day seven, the mortality rate drops to 14-23%. Newborns are at increased risk for Group B disease if they are born to women who are colonized with Group B streptococci in the vaginal or anorectal areas and who experience prolonged or difficult labor and delivery. As a strategy for prevention of Group B disease, the CDC has recommended that all pregnant women be screened for anogenital Group B colonization at 35 to 37 weeks gestation, so that intrapartum antimicrobial prophylaxis can be offered to all women identified as carriers. Screening is accomplished by obtaining vaginal and/or anorectal swabs and culturing them in recommended media such as Lim broth, incubated for 18 to 24 hours. Group B *Streptococcus* can also cause serious illness in adults but it far less common than in newborns.

Presumptive identification of *Streptococcus agalactiae* was traditionally made by physiological and biochemical methods. These include gram strain, catalase reaction, hemolytic activity on sheep blood agar plates, hippurate or L-pyrrolidonyl-β-naphthylamide (PYR) hydrolysis, CAMP and bile esculin tests. Because some Group B *Streptococcus* colonies are non-hemolytic on sheep blood agar, confirmative identification of Group B *Streptococcus* required a combination of biochemical tests and/or serological tests.

More recently, DNA probe tests have aided in the identification of Group B *Streptococcus* from culture. The DNA probe tests use nucleic acid hybridization for the qualitative detection of Group B Streptococcal DNA and RNA. Such tests offer a non-subjective, accurate and rapid identification method for definitively identifying *Streptococcus agalactiae*.

The present invention improves upon the DNA probe tests by: increasing the sensitivity, precision and specific detection of Group B streptococci; providing for the ability of qualitative and quantitative measurements; and, increasing the speed of detection of low target copy levels due to the combination of amplification and detection in real-time.

SUMMARY OF THE INVENTION

A first aspect of the invention relates to a hybridization assay probe for detecting a *Streptococcus agalactiae* nucleic acid, This hybridization assay probe includes a probe sequence that has a target-complementary sequence of bases, and optionally one or more base sequences that are not complementary to the nucleic acid that is to be detected. The target-complementary sequence of bases consists of 16-20 contiguous bases contained within the sequence of SEQ ID NO:3, or the complement thereof, allowing for the presence of RNA and DNA equivalents and nucleotide analogs. In general, the hybridization assay probe can have a length of up to 30 bases. In a preferred embodiment, the probe sequence includes the optional base sequences that are not complementary to the nucleic acid that is to be detected. More preferably, the hybridization assay probe includes a detectable label. For example, the probe may include a fluorophore moiety and a quencher moiety. In such an instance, the hybridization assay probe can be a molecular beacon. An exemplary molecular beacon can include a target-complementary sequence of bases selected from the group consisting of SEQ ID NO:14, SEQ ID NO:15, SEQ ID NO:16 and SEQ ID NO:17. In accordance with another preferred embodiment, the probe sequence does not include the optional base sequences that are not complementary to the nucleic acid that is to be detected. More preferably, the hybridization assay probe includes a detectable label. This detectable label can be either a chemiluminescent label or a fluorescent label.

Another aspect of the invention relates to a kit for amplifying a *Streptococcus agalactiae* nucleic acid sequence that may be present in a biological sample. The kit contains a first primer that has a 3' terminal target-complementary sequence, and optionally a first primer upstream sequence that is not complementary to the target nucleic acid sequence that is to be amplified. The 3' terminal target-complementary sequence of this first primer includes 25 contiguous bases contained within SEQ ID NO:2, allowing for the presence of RNA and DNA equivalents and nucleotide analogs. Also included in the kit is a second primer that has a 3' terminal target-complementary sequence, and optionally a second primer upstream sequence that is not complementary to the target nucleic acid sequence that is to be amplified. The 3' terminal target-complementary sequence of the second primer includes 20 contiguous bases contained within SEQ ID NO: 1, allowing for the presence of RNA and DNA equivalents and nucleotide analogs. In a preferred embodiment of the kit, the first primer and the second primer are each up to 58 bases in length. In another preferred embodiment, the 3' terminal target-complementary sequence of the first primer and the 3' terminal target-complementary sequence of the second primer are each up to 31 bases in length. When this is the case, it is more preferable for the 3' terminal target-complementary sequence of the second primer to be up to 21 bases in length. Still more preferably, the first primer includes a first primer upstream sequence, such as a promoter sequence for T7 RNA polymerase. In accordance with another preferred embodiment of the kit, when the 3' terminal target-complementary sequence of the first primer is up to 31 bases in length, and when the 3' terminal target-complementary sequence of the second primer is up to 21 bases in length, the 3' terminal target-complementary sequence of the first primer is preferably selected from the group consisting of SEQ ID NO:8, SEQ ID NO:9 and SEQ ID NO:10, and the 3' terminal target-complementary sequence of the second primer is preferably selected from the group consisting of SEQ ID NO:4, SEQ ID NO:5 and SEQ ID NO:6.

DEFINITIONS

The following terms have the following meanings for the purpose of this disclosure, unless expressly stated to the contrary herein.

As used herein, a "biological sample" is any tissue or polynucleotide-containing material obtained from a human, animal, or environmental sample. Biological samples in accordance with the invention include peripheral blood, plasma, serum or other body fluid, bone marrow or other organ, biopsy tissues, or other materials of biological origin. A biological sample may be treated to disrupt tissue or cell structure, thereby releasing intracellular components into a solution which may contain enzymes, buffers, salts, detergents, and the like.

As used herein, "polynucleotide" means either RNA or DNA, along with any synthetic nucleotide analogs or other molecules that may be present in the sequence and that do not prevent hybridization of the polynucleotide with a second molecule having a complementary sequence.

As used herein, a "detectable label" is a chemical species that can be detected or can lead to a detectable response. Detectable labels in accordance with the invention can be linked to polynucleotide probes either directly or indirectly, and include radioisotopes, enzymes, haptens, chromophores such as dyes or particles that impart a detectable color (e.g., latex beads or metal particles), luminescent compounds (e.g., bioluminescent, phosphorescent or chemiluminescent moieties), and fluorescent compounds.

A "homogeneous detectable label" refers to a label that can be detected in a homogeneous fashion by determining whether the label is on a probe hybridized to a target sequence. That is, homogeneous detectable labels can be detected without physically removing hybridized from unhybridized forms of the label or labeled probe. Homogeneous detectable labels are preferred when using labeled probes for detecting GBS nucleic acids. Examples of homogeneous labels have been described in detail by Arnold et al., U.S. Pat. No. 5,283,174; Woodhead et al., U.S. Pat. No. 5,656,207; and, Nelson et al., U.S. Pat. No. 5,658,737. Preferred labels for use in homogenous assays include chemiluminescent compounds (see, e.g., Woodhead et al., U.S. Pat. No. 5,656,207; Nelson et al., U.S. Pat. No. 5,658,737; and, Arnold et al., U.S. Pat. No. 5,639,604). Preferred chemiluminescent labels are acridinium ester (AE) compounds, such as standard AE or derivatives thereof (e.g., naphthyl-AE, ortho-AS, 1- or 3-methyl-AH, 2,7-dimethyl-AE, 4,5-dimethyl-AE, ortho-dibromo-AE, ortho-dimethyl-AE, meta-dimethyl-AS, ortho-methoxy-AE, ortho-methoxy(cinnamyl)-AE, ortho-methyl-AE, ortho-fluoro-AE, 1- or 3-methyl-ortho-fluoro-AE, 1- or 3-methyl-meta-difluoro-AE, and 2-methyl-AE).

A "homogeneous assay" refers to a detection procedure that does not require physical separation of hybridized probe from unhybridized probe prior to determining the extent of specific probe hybridization. Exemplary homogeneous assays, such as those described herein, can employ molecular beacons or other self-reporting probes that emit fluorescent signals when hybridized to an appropriate target, chemiluminescent acridinium ester labels that can be selectively destroyed by chemical means unless present in a hybrid duplex, and other homogeneously detectable labels that will be familiar to those having an ordinary level of skill in the art.

As used herein, "amplification" refers to an in vitro procedure for obtaining multiple copies of a target nucleic acid sequence, its complement or fragments thereof.

By "target nucleic acid" or "target" is meant a nucleic acid containing a target nucleic acid sequence. In general, a target nucleic acid sequence that is to be amplified will be positioned between two oppositely disposed primers, and will include the portion of the target nucleic acid that is fully complementary to each of the primers.

By "target nucleic acid sequence" or "target sequence" or "target region" is meant a specific deoxyribonucleotide or ribonucleotide sequence comprising all or part of the nucleotide sequence of a single-stranded nucleic acid molecule, and the deoxyribonucleotide or ribonucleotide sequence complementary thereto.

By "transcription associated amplification" is meant any type of nucleic acid amplification that uses an RNA polymerase to produce multiple RNA transcripts from a nucleic acid template. One example of a transcription associated amplification method, called "Transcription Mediated Amplification" (TMA), generally employs an RNA polymerase, a DNA polymerase, deoxyribonucleoside triphosphates, ribonucleoside triphosphates, and a promoter-template complementary oligonucleotide, and optionally may include one or more analogous oligonucleotides. Variations of TMA are well known in the art as disclosed in detail in Burg et al., U.S. Pat. No. 5,437,990; Kacian et al., U.S. Pat. Nos. 5,399,491 and 5,554,516; Kacian et al., PCT Int'l Publ. No. WO 93/22461; Gingeras et al., PCT Int'l Publ. No. WO 88/01302; Gingeras et al., PCT Int'l Publ. No. WO 88/10315; Malek et al., U.S. Pat. No. 5,130,238; Urdea et al., U.S. Pat. Nos. 4,868,105 and 5,124,246; McDonough et al., PCT Int'l Publ. No. WO 94/03472; and, Ryder et al., PCT Int'l Publ. No. WO 95/03430. The methods of Kacian et al. are preferred for conducting nucleic acid amplification procedures of the type disclosed herein.

As used herein, an "oligonucleotide" or "oligomer" is a polymeric chain of at least two, generally between about five and about 100, chemical subunits, each subunit comprising a nucleotide base moiety, a sugar moiety, and a linking moiety that joins the subunits in a linear spacial configuration. Common nucleotide base moieties are guanine (G), adenine (A), cytosine (C), thymine (T) and uracil (U), although other rare or modified nucleotide bases able to hydrogen bond are well known to those skilled in the art. Oligonucleotides may optionally include analogs of any of the sugar moieties, the base moieties, and the backbone constituents. Preferred oligonucleotides of the present invention fall in a size range of about 10 to about 100 residues. Oligonucleotides may be purified from naturally occurring sources, but preferably are synthesized using any of a variety of well known enzymatic or chemical methods.

As used herein, a "probe" is an oligonucleotide that hybridizes specifically to a target sequence in a nucleic acid, preferably in an amplified nucleic acid, under conditions that promote hybridization, to form a detectable hybrid. A probe optionally may contain a detectable moiety which either may be attached to the end(s) of the probe or may be internal. The nucleotides of the probe that combine with the target polynucleotide need not be strictly contiguous, as may be the case with a detectable moiety internal to the sequence of the probe. Detection may either be direct (i.e., resulting from a probe hybridizing directly to the target sequence or amplified nucleic acid) or indirect (i.e., resulting from a probe hybridizing to an intermediate molecular structure that links the probe to the target sequence or amplified nucleic acid). The "target" of a probe generally refers to a sequence contained within an amplified nucleic acid sequence which hybridizes specifically to at least a portion of a probe oligonucleotide using standard hydrogen bonding (i.e., base pairing). A probe may comprise target-specific sequences and optionally other sequences that are non-complementary to the target sequence that is to be detected. These non-complementary sequences may comprise a promoter sequence, a restriction endonuclease recognition site, or sequences that contribute to three-dimensional conformation of the probe (see, e.g., Lizardi et al., U.S. Pat. Nos. 5,118,801 and 5,312,728). Sequences that are "sufficiently complementary" allow stable hybridization of a probe oligonucleotide to a target sequence that is not completely complementary to the probe's target-specific sequence.

As used herein, an "amplification primer" is an oligonucleotide that hybridizes to a target nucleic acid, or its complement, and participates in a nucleic acid amplification reaction. For example, amplification primers, or more simply "primers," may be optionally modified oligonucleotides that are capable of hybridizing to a template nucleic acid and that have a 3' end that can be extended by a DNA polymerase activity. In general, a primer will have a downstream sequence that is complementary to GBS nucleic acids, and optionally an upstream sequence that is not complementary to GBS nucleic acids. The optional upstream sequence may, for example, serve as an RNA polymerase promoter or contain restriction endonuclease cleavage sites.

By "substantially homologous," "substantially corresponding" or "substantially corresponds" is meant that the subject oligonucleotide has a base sequence containing an at least 10 contiguous base region that is at least 70% homologous, preferably at least 80% homologous, more preferably at least 90% homologous, and most preferably 100% homologous, to an at least 10 contiguous base region present in a reference base sequence (excluding RNA and DNA equivalents). Those skilled in the art will readily appreciate modifications that could be made to the hybridization assay conditions at various percentages of homology to permit hybridization of the oligonucleotide to the target sequence while preventing unacceptable levels of non-specific hybridization. The degree of similarity is determined by comparing the order of nucleobases making up the two sequences and does not take into consideration other structural differences which may exist between the two sequences, provided the structural differences do not prevent hydrogen bonding with complementary bases. The degree of homology between two sequences can also be expressed in terms of the number of base mismatches present in each set of at least 10 contiguous bases being compared, which may range from 0-2 base differences.

By "substantially complementary" is meant that the subject oligonucleotide has a base sequence containing an at least 10 contiguous base region that is at least 70% complementary, preferably at least 80% complementary, more preferably at least 90% complementary, and most preferably 100% complementary, to an at least 10 contiguous base region present in a target nucleic acid sequence (excluding RNA and DNA equivalents). Those skilled in the art will readily appreciate modifications that could be made to the hybridization assay conditions at various percentages of complementarity to permit hybridization of the oligonucleotide to the target sequence while preventing unacceptable levels of non-specific hybridization. The degree of complementarity is determined by comparing the order of nucleobases making up the two sequences and does not take into consideration other structural differences which may exist between the two sequences, provided the structural differences do not prevent hydrogen bonding with complementary bases. The degree of complementarity between two sequences can also be expressed in terms of the number of base mismatches present in each set of at least 10 contiguous bases being compared, which may range from 0-2 base mismatches.

By "sufficiently complementary" is meant a contiguous nucleic acid base sequence that is capable of hybridizing to another base sequence by hydrogen bonding between a series of complementary bases. Complementary base sequences may be complementary at each position in the base sequence of an oligonucleotide using standard base pairing (e.g., G:C, A:T or A:U pairing) or may contain one or more residues that are not complementary using standard hydrogen bonding (including abasic nucleotides), but in which the entire complementary base sequence is capable of specifically hybridizing with another base sequence under appropriate hybridization conditions. Contiguous bases are preferably at least about 80%, more preferably at least about 90%, and most preferably about 100%, complementary to a sequence to which an oligonucleotide is intended to specifically hybridize. Appropriate hybridization conditions are well known to those skilled in the art, can be predicted readily based on base sequence composition, or can be determined empirically by using routine testing (see, e.g., Sambrook et al., *Molecular Cloning: A Laboratory Manual*, $2^{nd}$ ed. (Cold Spring Harbor Laboratory Press, Cold Spring Harbor, N.Y., 1989) at §§1.90-1.91, 7.37-7.57, 9.47-9.51 and 11.47-11.57, particularly at §§9.50-9.51, 11.12-11.13, 11.45-11.47 and 11.55-11.57).

By "capture oligonucleotide" is meant at least one nucleic acid oligonucleotide that provides means for specifically joining a target sequence and an immobilized oligonucleotide due to base pair hybridization. A capture oligonucleotide preferably includes two binding regions: a target sequence-binding region and an immobilized probe-binding region. Usually the two binding regions are contiguous on the same oligonucleotide, although the capture oligonucleotide may include a target sequence-binding region and an immobilized probe-binding region that are present on two different oligonucleotides joined together by one or more linkers. For example, an immobilized probe-binding region may be present on a first oligonucleotide, the target sequence-binding region may be present on a second oligonucleotide, and the two different oligonucleotides are joined by hydrogen bonding with a linker that is a third oligonucleotide containing sequences that hybridize specifically to the sequences of the first and second oligonucleotides.

By "immobilized probe" or "immobilized nucleic acid" is meant a nucleic acid that joins, directly or indirectly, a capture oligonucleotide to an immobilized support. An immobilized probe is an oligonucleotide joined to a solid support that facilitates separation of bound target sequence from unbound material in a sample.

By "separating" or "purifying" is meant that one or more components of the biological sample are removed from one or more other components of the sample. Sample components include nucleic acids in a generally aqueous solution phase which may also include materials such as proteins, carbohydrates, lipids, and labeled probes. Preferably, the separating or purifying step removes at least about 70%, more preferably at least about 90%, and even more preferably at least about 95%, of the other components present in the sample.

By "RNA and DNA equivalents" or "RNA and DNA equivalent bases" is meant molecules, such as RNA and DNA, having the same complementary base pair hybridization properties. RNA and DNA equivalents have different sugar moieties (i.e., ribose versus deoxyribose) and may differ by the presence of uracil in RNA and thymine in DNA. The differences between RNA and DNA equivalents do not contribute to differences in homology because the equivalents have the same degree of complementarity to a particular sequence.

By "consisting essentially of" is meant that additional component(s), composition(s) or method step(s) that do not materially change the basic and novel characteristics of the present invention may be included in the compositions or kits or methods of the present invention. Such characteristics include the ability to selectively detect GBS nucleic acids in biological samples such as whole blood or plasma. Any component(s), composition(s) or method step(s) that have a material effect on the basic and novel characteristics of the present invention would fall outside of this term.

DETAILED DESCRIPTION OF THE INVENTION

Figure 1:
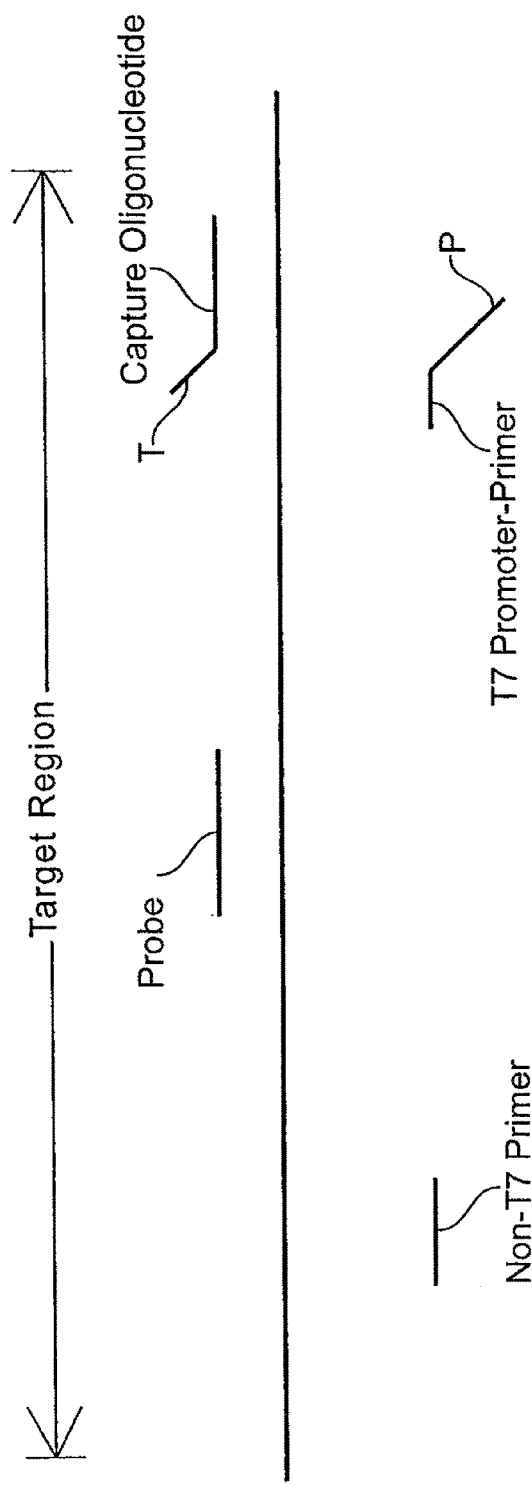
FIG. 1 is a schematic diagram illustrating the various polynucleotides that can be used for detecting a target region within the GBS nucleic acid (represented by a thick horizontal line). Positions of the following nucleic acids are shown relative to the target region: "Non-T7 Primer" and "T7 Promoter-Primer" represent two amplification primers used for conducting TMA, where "P" indicates the promoter sequence of the T7 promoter-primer; and "Probe" refers to the probe used for detecting amplified nucleic acid.

Disclosed herein are compositions, methods and kits for selectively detecting GBS nucleic acids in biological samples such as blood, plasma, serum or other body fluid, or tissue. The primers, probes and methods of the invention can be used in diagnostic applications.

Introduction and Overview

The present invention includes compositions (primers and probes), methods and kits that are particularly useful for detecting GBS nucleic acids in a biological sample. To design oligonucleotide sequences appropriate for such uses, known GBS nucleic acid sequences were first compared to identify candidate regions of the bacterial genome that could serve as targets in a diagnostic assay. As a result of these comparisons, three different regions of the GBS genome (SEQ ID NOs:1-3) were selected as targets for detection using the primers and probes shown schematically in FIG. 1. Portions of sequences containing relatively few variants between the compared sequences were chosen as starting points for designing synthetic oligonucleotides suitable for use in amplification and detection of amplified sequences.

Based on these analyses, the amplification primer and probe sequences presented below were designed. Those having an ordinary level of skill in the art will appreciate that any primer sequences specific for GBS or other bacterial target, with or without a T7 promoter sequence, may be used as primers in the various primer-based in vitro amplification methods described below. It is also contemplated that oligonucleotides having the sequences disclosed herein could serve alternative functions in assays for detecting GBS nucleic acids. For example, the hybridization probes disclosed herein could be used as amplification primers, and the amplification primers disclosed herein could be used as hybridization probes in alternative detection assays. It is further contemplated that capture oligonucleotides may be used to hybridize to and capture a target nucleic acid prior to amplification.

The amplification primers disclosed herein are particularly contemplated as components of multiplex amplification reactions wherein several amplicon species can be produced from an assortment of target-specific primers. For example, it is contemplated that certain preferred GBS-specific primers disclosed herein can be used in multiplex amplification reactions that are capable of amplifying polynucleotides of unrelated bacteria without substantially compromising the sensitivities of those assays.

Useful Amplification Methods

Amplification methods useful in connection with the present invention include Transcription Mediated Amplification (TMA), Nucleic Acid Sequence-Based Amplification (NASBA), the Polymerase Chain Reaction (PCR), Strand Displacement Amplification (SDA), and amplification methods using self-replicating polynucleotide molecules and replication enzymes such as MDV-1 RNA and Q-beta enzyme. Methods for carrying out these various amplification techniques can be found respectively in U.S. Pat. No. 5,399,491; published European Patent Appl. No. EP 0 525 882; U.S. Pat. No. 4,965,188; U.S. Pat. No. 5,455,166; U.S. Pat. No. 5,472,840; and, Lizardi et al., *BioTechnology* 6:1197 (1988). The disclosures of these documents which describe how to perform nucleic acid amplification reactions are hereby incorporated by reference.

In a highly preferred embodiment of the invention, GBS nucleic acid sequences are amplified using a TMA protocol. According to this protocol, the reverse transcriptase which provides the DNA polymerase activity also possesses an endogenous RNase H activity. One of the primers used in this procedure contains a promoter sequence positioned upstream of a sequence that is complementary to one strand of a target nucleic acid that is to be amplified. In the first step of the amplification, a promoter-primer hybridizes to the GBS target at a defined site. Reverse transcriptase creates a complementary DNA copy of the target RNA by extension from the 3' end of the promoter-primer. Following interaction of an opposite strand primer with the newly synthesized DNA strand, a second strand of DNA is synthesized from the end of the primer by reverse transcriptase, thereby creating a double-stranded DNA molecule. RNA polymerase recognizes the promoter sequence in this double-stranded DNA template and initiates transcription. Each of the newly synthesized RNA amplicons re-enters the TMA process and serves as a template for a new round of replication, thereby leading to an exponential expansion of the RNA amplicon. Since each of the DNA templates can make 100-1000 copies of RNA amplicon, this expansion can result in the production of 10 billion amplicons in less than one hour. The entire process is autocatalytic and is performed at a constant temperature.

Structural Features of Primers

As indicated above, a "primer" refers to an optionally modified oligonucleotide that is capable of participating in a nucleic acid amplification reaction. Preferred primers are capable of hybridizing to a template nucleic acid and have a 3' end that can be extended by a DNA polymerase activity. The 5' region of the primer may be non-complementary to the target nucleic acid. If the 5' non-complementary region includes a promoter sequence, it is referred to as a "promoter-primer." Those skilled in the art will appreciate that any oligonucleotide that can function as a primer (i.e., an oligonucleotide that hybridizes specifically to a target sequence and has a 3', end capable of extension by a DNA polymerase activity) can be modified to include a 5' promoter sequence, and thus could function as a promoter-primer. Similarly, any promoter-primer can be modified by removal of, or synthesis without, a promoter sequence and still function as a primer.

Nucleotide base moieties of primers may be modified (e.g., by the addition of propyne groups), so long as the modified base moiety retains the ability to form a non-covalent association with G, A, C, T or U, and so long as an oligonucleotide comprising at least one modified nucleotide base moiety or analog is not sterically prevented from hybridizing with a single-stranded nucleic acid. As indicated below in connection with the chemical composition of useful probes, the nitrogenous bases of primers in accordance with the invention may be conventional bases (A, G, C, T, U), known analogs thereof (e.g., inosine or "I" having hypoxanthine as its base moiety; see *The Biochemistry of the Nucleic Acids* 5-36, Adams et al., ed., 11$^{th}$ ed., 1992), known derivatives of purine or pyrimidine bases (e.g., N$^4$-methyl deoxyguanosine, deaza- or aza-purines and deaza- or aza-pyrimidines, pyrimidine bases having substituent groups at the 5 or 6 position, purine bases having an altered or a replacement substituent at the 2, 6 or 8 positions, 2-amino-6-methylaminopurine, O$^6$-methylguanine, 4-thio-pyrimidines, 4-amino-pyrimidines, 4-dimethylhydrazine-pyrimidines, and O$^4$-alkyl-pyrimidines (see Cook, PCT Int'l Pub. No. WO 93/13121)), and "abasic" residues where the backbone includes no nitrogenous base for one or more residues of the polymer (see Arnold et al., U.S. Pat. No. 5,585,481). Common sugar moieties that comprise the primer backbone include ribose and deoxyribose, although 2'-O-methyl ribose (2'-OMe), halogenated sugars, and other modified sugar moieties may also be used. Usually, the linking group of the primer backbone is a phosphorus-containing moiety, most commonly a phosphodiester linkage, although other linkages, such as, for example, phosphorothioates, methylphosphonates, and non-phosphorus-containing linkages such as the linkages found in "locked nucleic acids" (LNA) and the peptide-like linkages found in "peptide nucleic acids" (PNA) also are intended for use in the assay disclosed herein.

Useful Probe Labeling Systems and Detectable Moieties

Essentially any labeling and detection system that can be used for monitoring specific nucleic acid hybridization can be used in conjunction with the present invention. Included among the collection of useful labels are radiolabels, enzymes, haptens, linked oligonucleotides, chemiluminescent molecules, fluorescent moieties (either alone or in combination with "quencher" moieties), and redox-active moieties that are amenable to electronic detection methods. Preferred chemiluminescent molecules include acridinium esters of the type disclosed in Arnold et al., U.S. Pat. No. 5,283,174 for use in connection with homogenous protection assays, and of the type disclosed in Woodhead et al., U.S. Pat. No. 5,656,207 for use in connection with assays that quantify multiple targets in a single reaction. The disclosures contained in these patent documents are hereby incorporated by reference. Preferred electronic labeling and detection approaches are disclosed in U.S. Pat. Nos. 5,591,578 and 5,770,369, and PCT Int'l Publ. No. WO 98/57158, the disclosures of which are hereby incorporated by reference. Redox active moieties useful as labels in the present invention include transition metals such as Cd, Mg, Cu, Co, Pd, Zn, Fe, and Ru.

Particularly preferred detectable labels for probes in accordance with the present invention are detectable in homogeneous assay systems (i.e., where, in a mixture, bound labeled probe exhibits a detectable change, such as stability or differential degradation, compared to unbound labeled probe). While other homogeneously detectable labels, such as fluorescent labels and electronically detectable labels, are intended for use in the practice of the present invention, a preferred label for use in homogenous assays is a chemiluminescent compound (e.g., as described in Woodhead et al., U.S. Pat. No. 5,656,207; Nelson et al., U.S. Pat. No. 5,658,737; or Arnold et al., U.S. Pat. No. 5,639,604). Particularly preferred chemiluminescent labels include acridinium ester (AE) compounds, such as standard AE or derivatives thereof, such as naphthyl-AE, ortho-AE, 1- or 3-methyl-AE, 2,7-dimethyl-AE, 4,5-dimethyl-AE, ortho-dibromo-AE, ortho-dimethyl-AE, meta-dimethyl-AE, ortho-methoxy-AE, ortho-methoxy (cinnamyl)-AE, ortho-methyl-AE, ortho-fluoro-AE, 1- or 3-methyl-ortho-fluoro-AE, 1- or 3-methyl-meta-difluoro-AE, and 2-methyl-AE. The acridinium ester can be joined to the probe by means of a non-nucleotide linker. For example, detection probes can be labeled with chemiluminescent acridinium ester compounds that are attached via a linker substantially as described in U.S. Pat. No. 5,585,481 and U.S. Pat. No. 5,639,604, particularly at column 10, line 6 to column 11, line 3, and Example 8. The disclosures contained in these patent documents are hereby incorporated by reference.

In some applications, probes exhibiting at least some degree of self-complementarity are desirable to facilitate detection of probe:target duplexes in a test sample without first requiring the removal of unhybridized probe prior to detection. By way of example, structures referred to as "molecular torches" are designed to include distinct regions of self-complementarity (coined "the target binding domain" and "the target closing domain") which are connected by a joining region and which hybridize to one another under predetermined hybridization assay conditions. When exposed to denaturing conditions, the two complementary regions of the molecular torch, which may be fully or partially complementary, melt, leaving the target binding domain available for hybridization to a target sequence when the predetermined hybridization assay conditions are restored. Molecular torches are designed so that the target binding domain favors hybridization to the target sequence over the target closing domain. The target binding domain and the target closing domain of a molecular torch include interacting labels (e.g., a fluorescent/quencher pair) positioned so that a different signal is produced when the molecular torch is self-hybridized as opposed to when the molecular torch is hybridized to a target nucleic acid, thereby permitting detection of probe:target duplexes in a test sample in the presence of unhybridized probe having a viable label associated therewith. Molecular torches are fully described in U.S. Pat. No. 6,361,945, the disclosure of which is hereby incorporated by reference.

Another example of a self-complementary hybridization assay probe that may be used in conjunction with the invention is a structure commonly referred to as a "molecular beacon." Molecular beacons comprise nucleic acid molecules having a target complementary sequence, an affinity pair (or nucleic acid arms) that holds the probe in a closed conformation in the absence of a target nucleic acid sequence, and a label pair that interacts when the probe is in a closed conformation. Hybridization of the molecular beacon target complementary sequence to the target nucleic acid separates the members of the affinity pair, thereby shifting the probe to an open conformation. The shift to the open conformation is detectable due to reduced interaction of the label pair, which may be, for example, a fluorophore and a quencher (e.g., DABCYL and EDANS). Molecular beacons are fully described in U.S. Pat. No. 5,925,517, the disclosure of which is hereby incorporated by reference. Molecular beacons useful for detecting GBS-specific nucleic acid sequences may be created by appending to either end of one of the probe sequences disclosed herein, a first nucleic acid arm comprising a fluorophore and a second nucleic acid arm comprising a quencher moiety, In this configuration, the GBS-specific probe sequence disclosed herein serves as the target-complementary "loop" portion of the resulting molecular beacon.

Molecular beacons are preferably labeled with an interactive pair of detectable labels. Preferred detectable labels interact with each other by FRET or non-FRET energy transfer mechanisms. Fluorescence resonance energy transfer (FRET) involves the radiationless transmission of energy quanta from the site of absorption to the site of its utilization in the molecule or system of molecules by resonance interaction between chromophores, over distances considerably greater than interatomic distances, without conversion to thermal energy, and without the donor and acceptor coming into kinetic collision. The "donor" is the moiety that initially absorbs the energy, and the "acceptor" is the moiety to which the energy is subsequently transferred. In addition to FRET, there are at least three other "non-FRET" energy transfer processes by which excitation energy can be transferred from a donor to an acceptor molecule.

When two labels are held sufficiently close such that energy emitted by one label can be received or absorbed by the second label, whether by a FRET or non-FRET mechanism, the two labels are said to be in an "energy transfer relationship." This is the case, for example, when a molecular beacon is maintained in the closed state by formation of a stem duplex and fluorescent emission from a fluorophore attached to one arm of the molecular beacon is quenched by a quencher moiety on the other arm.

Highly preferred label moieties for the invented molecular beacons include a fluorophore and a second moiety having fluorescence quenching properties (i.e., a "quencher"). In this embodiment, the characteristic signal is likely fluorescence of a particular wavelength, but alternatively could be a visible light signal. When fluorescence is involved, changes in emission are preferably due to FRET, or to radiative energy transfer or non-FRET modes. When a molecular beacon having a pair of interactive labels in the closed state is stimulated by an appropriate frequency of light, a fluorescent signal is generated at a first level, which may be very low. When this same molecular beacon is in the open state and is stimulated by an appropriate frequency of light, the fluorophore and the quencher moieties are sufficiently separated from each other such that energy transfer between them is substantially precluded. Under that condition, the quencher moiety is unable to quench the fluorescence from the fluorophore moiety. If the fluorophore is stimulated by light energy of an appropriate wavelength, a fluorescent signal of a second level, higher than the first level, will be generated. The difference between the two levels of fluorescence is detectable and measurable. Using fluorophore and quencher moieties in this manner, the molecular beacon is only "on" in the "open" conformation and indicates that the probe is bound to the target by emanating an easily detectable signal. The conformational state of the probe alters the signal generated from the probe by regulating the interaction between the label moieties.

Examples of donor/acceptor label pairs that may be used in connection with the invention, making no attempt to distinguish FRET from non-FRET pairs, include fluorescein/tetramethylrhodamine, IAEDANS/fluorescein, EDANS/DABCYL, coumarin/DABCYL, fluorescein/fluorescein, BODIPY FL/BODIPY FL, fluorescein/DABCYL, lucifer yellow/DABCYL, BODIPY/DABCYL, eosine/DABCYL, erythrosine/DABCYL, tetramethylrhodamine/DABCYL, Texas Red/DABCYL, CY5/BH1, CY5/BH2, CY3/BH1, CY3/BH2, and fluorescein/QSY7 dye. Those having an ordinary level of skill in the art will understand that when donor and acceptor dyes are different, energy transfer can be detected by the appearance of sensitized fluorescence of the acceptor or by quenching of donor fluorescence. When the donor and acceptor species are the same, energy can be detected by the resulting fluorescence depolarization. Non-fluorescent acceptors such as DABCYL and the QSY 7 dyes advantageously eliminate the potential problem of background fluorescence resulting from direct (i.e., non-sensitized) acceptor excitation. Preferred fluorophore moieties that can be used as one member of a donor-acceptor pair include fluorescein, ROX, and the CY dyes (such as CY5). Highly preferred quencher moieties that can be used as another member of a donor-acceptor pair include DABCYL and the BLACK HOLE QUENCHER moieties which are available from Biosearch Technologies, Inc. (Novato, Calif.).

Synthetic techniques and methods of bonding labels to nucleic acids and detecting labels are well known in the art (see, e.g., Sambrook et al., *Molecular Cloning: A Laboratory*

Manual, 2nd ed. (Cold Spring Harbor Laboratory Press, Cold Spring Harbor, N.Y., 1989), Chapter 10; Nelson et al., U.S. Pat. No. 5,658,737; Woodhead et al., U.S. Pat. No. 5,656,207; Hogan et al., U.S. Pat. No. 5,547,842; Arnold et al., U.S. Pat. No. 5,283,174; Kourilsky et al., U.S. Pat. No. 4,581,333; and, Becker et al., European Patent Appl. No. EP 0 747 706).

Chemical Composition of Probes

Probes in accordance with the invention comprise polynucleotides or polynucleotide analogs, and optionally carry a detectable label covalently bound thereto. Nucleosides or nucleoside analogs of the probe comprise nitrogenous heterocyclic bases or base analogs, where the nucleosides are linked together, for example, by phosphodiester bonds to form a polynucleotide. Accordingly, a probe may comprise conventional ribonucleic acid (RNA) and/or deoxyribonucleic acid (DNA), but also may comprise chemical analogs of these molecules. The probe backbone may be made up from a variety of linkages known in the art, including one or more sugar-phosphodiester linkages, locked nucleic acid (LNA) bonds, peptide-nucleic acid bonds (sometimes referred to as "peptide nucleic acids" as described in Hyldig-Nielsen et al., PCT Int'l Publ. No. WO 95/32305), phosphorothioate linkages, methylphosphonate linkages, or combinations thereof. Sugar moieties of the probe may be either ribose or deoxyribose, or similar compounds having known substitutions, such as, for example, 2'-O-methyl ribose and 2' halide substitutions (e.g., 2'-F). The nitrogenous bases may be conventional bases (A, G, C, T, U), known analogs thereof (e.g., inosine or "I"; see *The Biochemistry of the Nucleic Acids* 5-36, Adams et al., ed., 11th ed., 1992), known derivatives of purine or pyrimidine bases (e.g., $N^4$-methyl deoxyguanosine, deaza- or aza-purines and deaza- or aza-pyrimidines, pyrimidine bases having substituent groups at the 5 or 6 position, purine bases having an altered or a replacement substituent at the 2, 6 or 8 positions, 2-amino-6-methylaminopurine, $O^6$-methylguanine, 4-thio-pyrimidines, 4-amino-pyrimidines, 4-dimethylhydrazine-pyrimidines, and $O^4$-alkyl-pyrimidines (see Cook, PCT Int'l Publ. No. WO 93/13121)), and "abasic" residues where the backbone includes no nitrogenous base for one or more residues of the polymer (see Arnold et al., U.S. Pat. No. 5,585,481). A probe may comprise only conventional sugars, bases and linkages found in RNA and DNA, or may include both conventional components and substitutions (e.g., conventional bases linked via a methoxy backbone, or a nucleic acid including conventional bases and one or more base analogs).

While oligonucleotide probes of different lengths and base composition may be used for detecting GBS nucleic acids, preferred probes in this invention have lengths of up to 30 nucleotides, and more preferably within the length range of 26 to 30 nucleotides. However, the specific probe sequences described below may also be provided in a nucleic acid cloning vector or transcript or other longer nucleic acid and still be used for detecting GBS nucleic acids.

Selection of GBS-Specific Amplification Primers and Detection Probes

Useful guidelines for designing amplification primers and probes with desired characteristics are described herein. The optimal sites for amplifying and probing GBS nucleic acids are three conserved regions of the GBS genome, each greater than about 20 bases in length, within about 250 bases of contiguous sequence. The degree of amplification observed with a set of primers, including one or more promoter-primers, depends on several factors including the ability of the oligonucleotides to hybridize to their complementary sequences and their ability to be extended enzymatically. Because the extent and specificity of hybridization reactions are affected by a number of factors, manipulation of those factors will determine the exact sensitivity and specificity of a particular oligonucleotide, whether perfectly complementary to its target or not. The effects of varying assay conditions are known to those skilled in the art, and are described in Hogan et al., U.S. Pat. No. 5,840,488, the disclosure of which is hereby incorporated by reference.

The length of the target nucleic acid sequence and, accordingly, the length of the primer sequence or probe sequence can be important. In some cases, there may be several sequences from a particular target region, varying in location and length, which will yield primers or probes having the desired hybridization characteristics. While it is possible for nucleic acids that are not perfectly complementary to hybridize, the longest stretch of perfectly homologous base sequence will normally determine hybrid stability.

Amplification primers and probes should be positioned to minimize the stability of an oligonucleotide:non-target nucleic acid hybrid. It is preferred that the amplification primers and probes are able to distinguish between target and non-target sequences. In designing primers and probes, the differences in melting temperature, represented by $T_m$ values, should be as large as possible (e.g., at least 2°, and preferably 5° C.).

The degree of non-specific extension (primer-dimer or non-target copying) can also affect amplification efficiency. For this reason, primers are selected to have low self- or cross-complementarity, particularly at the 3' ends of the sequence. Long homopolymer tracts and high GC content are avoided to reduce spurious primer extension. Commercially available computer software can aid in this aspect of the design. Available computer programs include MacDNA-SIS™ 2.0 (Hitachi Software Engineering American Ltd.) and OLIGO ver. 6.6 (Molecular Biology Insights; Cascade, Colo.).

Those having an ordinary level of skill in the art will appreciate that hybridization involves the association of two single strands of complementary nucleic acid to form a hydrogen bonded double strand. It is implicit that if one of the two strands is wholly or partially involved in a hybrid, then that strand will be less able to participate in formation of a new hybrid. By designing primers and probes so that substantial portions of the sequences of interest are single stranded, the rate and extent of hybridization may be greatly increased. If the target is an integrated genomic sequence, then it will naturally occur in a double stranded form (as is the case with the product of the polymerase chain reaction). These double-stranded targets are naturally inhibitory to hybridization with a probe and require denaturation prior to the hybridization step.

The rate at which a polynucleotide hybridizes to its target is a measure of the thermal stability of the target secondary structure in the target-binding region. The standard measurement of hybridization rate is the $C_0t_{1/2}$, which is measured as moles of nucleotide per liter multiplied by seconds. Thus, it is the concentration of probe multiplied by the time at which 50% of maximal hybridization occurs at that concentration. This value is determined by hybridizing various amounts of polynucleotide to a constant amount of target for a fixed time. The $C_0t_{1/2}$ is found graphically by standard procedures familiar to those having an ordinary level of skill in the art.

Preferred Amplification Primers

Primers useful for conducting amplification reactions can have different lengths to accommodate the presence of extraneous sequences that do not participate in target binding and that may not substantially affect amplification or detection procedures. For example, promoter-primers useful for performing amplification reactions in accordance with the invention have at least a minimal sequence that hybridizes to the GBS target nucleic acid and a promoter sequence positioned upstream of that minimal sequence. However, insertion of sequences between the target binding sequence and the promoter sequence could change the length of the primer without compromising its utility in the amplification reaction. Additionally, the lengths of the amplification primers and probes are matters of choice so long as the sequences of these oligonucleotides conform to the minimal essential requirements for hybridizing the desired complementary sequence.

Tables 1 and 2 present specific examples of oligonucleotide sequences that were used as primers for amplifying GBS nucleic acids. Table 1 presents the sequences of GBS target-complementary primers to one strand of the GBS nucleic acid. All of the illustrative primers presented in Table 1 have target-complementary sequences contained within the sequence of SEQ ID NO:1.

TABLE 1

Oligonucleotide Sequences of Amplification Primers

| Sequence | SEQ ID NO: |
|---|---|
| AAGTGTCTGGTCAAACAGTGA | SEQ ID NO: 4 |
| TGGTCAAACAGTGAGGTGTGA | SEQ ID NO: 5 |
| GTGAGGTGTGATATGAGTCA | SEQ ID NO: 6 |

Table 2 presents the sequences of both the GBS target-complementary primers and the corresponding promoter-primers to the opposing strand of the GBS nucleic acid. As indicated above, all promoter-primers included sequences complementary to a GBS target sequence at their 3' ends and the T7 promoter sequence AATTTAATACGACTCACTATAGGGAGA (SEQ ID NO:7) at their 5' ends. Primers identified by SEQ ID NOs:11-13 in Table 2 are promoter-primers corresponding to the GBS target-complementary primers identified as SEQ ID NOs:8-10, respectively. All of the illustrative primers presented in Table 2 have target-complementary sequences contained within the sequence of SEQ ID NO:2.

TABLE 2

Oligonucleotide Sequences of Amplification Primers

| Sequence | SEQ ID NO: |
|---|---|
| TCCTTAACGAGAGTTCTCTCGCTCA | SEQ ID NO: 8 |
| GGGCCATTTTGCCGAGTTCCTTAACGAGA | SEQ ID NO: 9 |
| AAGTTACGGGGCCATTTTGCCGAGTTCCTTA | SEQ ID NO: 10 |
| AATTTAATACGACTCACTATAGGGAGATCCTTAACGAGAGTTCTCTCGCTCA | SEQ ID NO: 11 |
| AATTTTAATACGACTCACTATAGGGAGAGGGCCATTTTGCCGAGTTCCTTAACGAGA | SEQ ID NO: 12 |
| AATTTAATACGACTCACTATAGGGAGAAAGTTACGGGGCCATTTTGCCGAGTTCCTTA | SEQ ID NO: 13 |

Preferred sets of primers for amplifying GBS nucleic acid sequences include a first primer that hybridizes a GBS target sequence, such as one of the primers listed in Table 2, and a second primer that is complementary to the sequence of an extension product of the first primer, such as one of the primers listed in Table 1. In a highly preferred embodiment, the first primer is a promoter-primer that includes a T7 promoter sequence at its 5' end.

Preferred Detection Probes

Another aspect of the invention relates to oligonucleotides that can be used as hybridization probes for detecting GBS nucleic acids. Methods for amplifying a target nucleic acid sequence present in a GBS nucleic acid can include an optional further step for detecting amplicons. This detection procedure includes a step for contacting a test sample with a hybridization assay probe that preferentially hybridizes to the target nucleic acid sequence, or the complement thereof, under stringent hybridization conditions, thereby forming a probe:target duplex that is stable for detection. Next there is a step for determining whether the hybrid is present in the test sample as an indication of the presence or absence of GBS nucleic acids in the test sample. This may involve detecting the probe:target duplex, and preferably involves homogeneous assay systems.

Hybridization assay probes useful for detecting GBS nucleic acid sequences include a sequence of bases substantially complementary to a GBS target nucleic acid sequence. Thus, probes of the invention hybridize to one strand of a GBS target nucleic acid sequence, or the complement thereof. These probes may optionally have additional bases outside of the targeted nucleic acid region, which may or may not be complementary to the GBS nucleic acid.

Preferred probes are sufficiently homologous to the target nucleic acid to hybridize under stringent hybridization conditions corresponding to about 60° C. and a salt concentration in the range of 0.6-0.9 M for probes labeled with chemiluminescent molecules and corresponding to about 42° C. and a salt concentration in the range of 20-100 mM for molecular beacon probes. Preferred salts include lithium, magnesium and potassium chlorides, but other salts such as sodium chloride and sodium citrate also can be used in the hybridization solution. Example high stringency hybridization conditions are alternatively provided by 0.48 M sodium phosphate buffer, 0.1% sodium dodecyl sulfate and 1 mM each of EDTA and EGTA, or by 0.6 M LiCl, 1% lithium lauryl sulfate, 60 mM lithium succinate and 10 mM each of EDTA and EGTA.

Probes in accordance with the invention have sequences complementary to, or corresponding to, a domain of the GBS genome. Molecular beacon probes that are preferred for detecting GBS nucleic acid sequences have a probe sequence, which includes the target-complementary sequence of bases together with any base sequences that are not complementary to the nucleic acid that is to be detected, in the length range of from 26-30 nucleotides. Specific molecular beacon probes that are preferred for detecting GBS nucleic acid sequences have target-complementary sequences in the length range of from 16-20 nucleotides. Of course, these target-complementary sequences may be linear sequences, or may be contained in the structure of a molecular beacon or other construct having one or more optional nucleic acid sequences that are non-complementary to the GBS target sequence that is to be detected. As indicated above, probes may be made of DNA, RNA, a combination DNA and RNA, a nucleic acid analog, or contain one or more modified nucleosides (e.g., a ribonucleoside having a 2'-O-methyl substitution to the ribofuranosyl moiety).

Simply stated, preferred probes for detecting target nucleic acids of interest in connection with the present invention include sequences that are contained within one or more of several defined probe domains, or the complements thereof, allowing for the presence of RNA and DNA equivalents and nucleotide analogs. For example, preferred hybridization assay probes for detecting CBS nucleic acids can include target-complementary sequences of bases contained within the sequence of SEQ ID NO:3. Optional sequences which are not complementary to the nucleic acid sequence that is to be detected may be linked to the target-complementary sequence of the probe.

Certain preferred probes in accordance with the present invention include a detectable label. This label includes a fluorophore and a second moiety having fluorescence quenching properties.

Table 3 presents the GBS target-complementary oligonucleotide sequences contained in the loop portions of the molecular beacon probes and the corresponding complete sequences of the molecular beacon probes used for detecting GBS amplicons. Each of the molecular beacons included a 5'CCGAG arm sequence and a 3'CUCGG arm sequence appended to the GBS target-complementary sequence contained in the loop portion of the molecular beacon. Loop portions identified by SEQ ID NOs:14-17 in Table 3 correspond to the molecular beacons identified as SEQ ID NOs: 18-21, respectively. All of the GBS-specific molecular beacons used in the procedure had target-complementary sequences that included 16-20 contiguous nucleotides contained within the sequence of SEQ ID NO:3, allowing for the presence of RNA and DNA equivalents. The target-complementary sequences presented in Table 3 were independently incorporated into the loop regions of molecular beacons. Each of the molecular beacons used in the procedure included a fluorescein fluorophore at its 5'-end and a DABCYL quencher moiety at its 3'-end.

TABLE 3

| Oligonucleotide Sequences of GBS-Specific Molecular Beacons | |
| --- | --- |
| Sequence | SEQ ID NO: |
| UACAUAUACUCUACCC | SEQ ID NO: 14 |
| AUACAUAUACUCUACCC | SEQ ID NO: 15 |
| GAUACAUAUACUCUACCC | SEQ ID NO: 16 |
| GCGAUACAUAUACUCUACCC | SEQ ID NO: 17 |
| <u>CCGAG</u>-UACAUAUACUCUACCC-<u>CUCGG</u> | SEQ ID NO: 18 |
| <u>CCGAG</u>-AUACAUAUACUCUACCC-<u>CUCGG</u> | SEQ ID NO: 19 |
| <u>CCGAG</u>-GAUACAUAUACUCUACCC-<u>CUCGG</u> | SEQ ID NO: 20 |
| <u>CCGAG</u>-GCGAUACAUAUACUCUACCC-<u>CUCGG</u> | SEQ ID NO: 21 |

Since alternative probes for detecting GBS nucleic acid sequences can hybridize to the opposite-sense GBS strand, the present invention also includes oligonucleotides that are complementary to the sequences presented in Table 3.

As indicated above, any number of different backbone structures can be used as a scaffold for the oligonucleotide sequences of the invented hybridization probes. In certain highly preferred embodiments, the probe sequence used for detecting GBS amplicons includes a methoxy backbone or at least one methoxy linkage in the nucleic acid backbone.

Preferred Methods for Amplifying and Detecting GBS Polynucleotide Sequences

Preferred methods of the present invention are described and illustrated by the Examples presented below. FIG. 1 schematically illustrates one system that may be used for detecting a target region of the GBS nucleic acid (shown by a thick solid horizontal line). This system includes at least three oligonucleotides (shown by the shorter solid lines): one T7 promoter-primer which includes a sequence that hybridizes specifically to a GBS sequence in the target region and a T7 promoter sequence ("P") which, when double-stranded, serves as a functional promoter for T7 RNA polymerase; one non-T7 primer which includes a sequence that hybridizes specifically to a first strand cDNA made from the target region sequence using the T7 promoter-primer; and, one labeled probe which includes a sequence that hybridizes specifically to a portion of the target region that is amplified using the two primers.

As indicated above, amplifying the target region using the two primers can be accomplished by any of a variety of known nucleic acid amplification reactions that will be familiar to those having an ordinary level of skill in the art. In a preferred embodiment, a transcription associated amplification reaction, such as TMA, is employed. In such an embodiment, many strands of nucleic acid are produced from a single copy of target nucleic acid, thus permitting detection of the target by detecting probes that are bound to the amplified sequences. Preferably, transcription associated amplification uses two types of primers (one being referred to as a promoter-primer because it contains a promoter sequence, labeled "P" in FIG. 1, for an RNA polymerase), two enzymes (a reverse transcriptase and an RNA polymerase), and substrates (deoxyribonucleoside triphosphates, ribonucleoside triphosphates) with appropriate salts and buffers in solution to produce multiple RNA transcripts from a nucleic acid template.

Referring to FIG. 1, during transcription mediated amplification, the target nucleic acid is hybridized to a first primer shown as a T7 promoter-primer. Using reverse transcriptase, a complementary DNA strand is synthesized from the T7 promoter-primer using the target RNA as a template. A second primer, shown as a non-T7 primer, hybridizes to the newly synthesized DNA strand and is extended by the action of a reverse transcriptase to form a DNA duplex, thereby forming a double-stranded T7 promoter region. T7 RNA polymerase then generates multiple RNA transcripts by using this functional T7 promoter. The autocatalytic mechanism of TMA employs repetitive hybridization and polymerization steps following a cDNA synthesis step using the RNA transcripts as templates to produce additional transcripts, thereby amplifying target region-specific nucleic acid sequences.

The detecting step uses at least one detection probe that binds specifically to the amplified RNA transcripts or amplicons described above. Preferably, the detection probe is labeled with a label that can be detected using a homogeneous detection system. For example, the labeled probe can be labeled with an acridinium ester compound from which a chemiluminescent signal may be produced and detected, as described above. Alternatively, the labeled probe may comprise a fluorophore, or fluorophore and quencher moieties. A molecular beacon is one embodiment of such a labeled probe that may be used in a homogeneous detection system.

Kits for Detecting GBS Nucleic Acids

The present invention also embraces kits for performing polynucleotide amplification reactions using bacterial nucleic acid templates. Certain preferred kits will contain a hybridization assay probe that includes a target-complementary sequence of bases, and optionally including primers or other ancillary oligonucleotides for amplifying the target that is to be detected. Other preferred kits will contain a pair of oligonucleotide primers that may be used for amplifying target nucleic acids in an in vitro amplification reaction. Exemplary kits include first and second amplification oligonucleotides that are complementary to opposite strands of a GBS nucleic acid sequence that is to be amplified. The kits may further contain one or more oligonucleotide detection probes. Still other kits in accordance with the invention may additionally include capture oligonucleotides for purifying GBS template nucleic acids away from other species prior to amplification.

The general principles of the present invention may be more fully appreciated by reference to the following non-limiting Examples.

Example 1 describes procedures that identified some of the hybridization probes, which subsequently were used in assays for detecting GBS nucleic acids. One synthetic RNA oligonucleotide served as a target for binding the probes.

Example 1

Oligonucleotides for Detecting GBS Nucleic Acids

Synthetic molecular beacons were prepared according to standard laboratory procedures using 2'-OMe nucleotide analogs. The sequences of the synthetic molecular beacons are shown in Table 3.

Hybridization reactions included 10 pmol/reaction of the molecular beacon and 30 pmol/reaction of the synthetic GBS RNA target oligonucleotide as given in Table 4.

TABLE 4

| Synthetic Target Sequence | |
|---|---|
| Target Sequence | SEQ ID NO: |
| GCGGUACGGGUAGAGUAUAUGUAUCGCUAGAAGCU | SEQ ID NO: 22 |

Hybridization reactions of the molecular beacons in the absence or presence of the synthetic GBS RNA target oligonucleotide were carried out at 60° C. for 10 minutes, followed by incubation at 42° C. for 60 minutes in 100 µl reaction volumes of a TRIS-buffered solution that included 20 mM $MgCl_2$.

Fluorescence was measured every 30 seconds at 42° C. for 99 cycles using a Rotor-Gene 2000 instrument (Corbett Research, Sydney, Australia). Results from the fluorescent reactions were measured in relative fluorescence units (RFU). After completion of the hybridization reactions, the reaction temperature was increased in one degree Celsius increments from 42-99° C. holding for 15 seconds at each step, and the resulting RFUs were measured to determine the melting temperatures ($T_m$) of the molecular beacons using the data analysis software provided by the Rotor-Gene 2000 instrument. Representative results for the hybridization reactions and melting temperature measurements are summarized in Table 5.

Numerical values shown in Table 5 indicate the average signal/noise (S/N) ratio values calculated from the measured endpoint RFUs in the presence of target divided by the measured endpoint RFUs in the absence of target. The calculated melting temperature of the molecular beacons in the absence of target is useful to determine the stability of the stem structure of the molecular beacon, whereas the melting temperature of the molecular beacon hybridized to the target sequence provides information about the stability of the hybrid.

TABLE 5

| Melting Temperatures and Hybrid Stability of Molecular Beacons | | | |
|---|---|---|---|
| Molecular Beacon | $T_m$ w/o Target (° C.) | $T_m$ w/Target (° C.) | S/N Ratio |
| SEQ ID NO: 18 | 73.7 | 62.9 | 28.4 |
| SEQ ID NO: 19 | 74.0 | 70.2 | 11.4 |
| SEQ ID NO: 20 | 85.4 | 67.8 | 15.7 |
| SEQ ID NO: 21 | 83.0 | 75.8 | 23.7 |

The results presented in Table 5 showed that each molecular beacon gave strong S/N ratio values following binding to the synthetic GBS RNA target oligonucleotide. In addition, the melting temperatures of the molecular beacons in the absence of target demonstrated that the molecular beacons have stable stem structures, which prevent unspecific "opening" of the molecular beacons at lower temperatures. The high melting temperatures of the molecular beacons in the presence of the synthetic GBS RNA target oligonucleotide showed that a stable hybrid was formed under the experimental conditions.

Amplicon production was monitored as a function of time in real-time amplification procedures Amplicon-specific molecular beacons that were included in the amplification reactions provided a means for continuous monitoring of amplicon synthesis. Fluorescent emissions that increased with time indicated the production of amplicons that hybridized to the molecular beacon and caused a detectable transition to the open conformation of the molecular beacon.

Molecular beacons comprise nucleic acid molecules having a target-complementary sequence, an affinity pair (or nucleic acid arms) that interact to form a stem structure by complementary base pairing in the absence of a target (i.e., the closed conformation), and a paired set of labels that interact when the probe is in the closed conformation. Those having an ordinary level of skill in the art will understand that the target-complementary sequence contained within the structure of a molecular beacon is generally in the form of a single-stranded loop region of the probe. Hybridization of the target nucleic acid and the target-complementary sequence of the probe causes the members of the affinity pair to separate, thereby shifting the probe to the open conformation. This shift is detectable by virtue of reduced interaction between the members of the label pair, which may be, for example, a fluorophore and a quencher. Molecular beacons are fully described in U.S. Pat. No. 5,925,517, the disclosure of this patent document being incorporated by reference herein.

Commercially available software was used to analyze time-dependent results obtained using molecular beacons that were specific for amplicons derived from the GBS nucleic acid. Results from these analyses indicated a substantially linear relationship between the number of target copies included in an amplification reaction and the time at which the fluorescent signal exceeded a background threshold (i.e., time-of-emergence). As confirmed by the results presented below, these procedures were useful for quantifying analyte target amounts over a very broad range. More particularly, when known amounts of analyte polynucleotides are used as calibration standards, it is possible to determine the amount of analyte present in a test sample by comparing the measured time-of-emergence with the standard curve.

The fact that the amplification reaction used in the below-described procedures operated at constant temperature and without interruption for a separate detection step, so that amplification and detection took place simultaneously, imposed strict requirements on the molecular beacons. More specifically, success in the procedure required that the molecular beacon bind amplicon without inhibiting subsequent use of the amplicon as a template in the exponential amplification mechanism. Indeed, the finding that an amplification reaction could proceed efficiently in the presence of a molecular beacon indicated that interaction of the probe with its target did not irreversibly inhibit or poison the amplification reaction.

Example 2 describes procedures wherein molecular beacon probes, each labeled with an interactive fluorophore/quencher pair, were used for monitoring time-dependent amplicon production in TMA reactions. Although the molecular beacons described in Example 2 hybridized to only one strand of the amplified nucleic acid product, complementary probe sequences also would be expected to hybridize to the opposite nucleic acid strand, and so fall within the scope of the invention.

Example 2

Real-Time Monitoring of Amplicon Production

Molecular beacons having binding specificity for the GBS amplicon were synthesized by standard solid-phase phosphite triester chemistry using 3' quencher-linked controlled pore glass (CPG) and 5' fluorophore-labeled phosphoramidite on a Perkin-Elmer (Foster City, Calif.) EXPEDITE model 8909 automated synthesizer, Fluorescein was used as the fluorophore, and DABCYL was used as the quencher for construction of the molecular beacons. All of the molecular beacons were constructed using 2'-OMe nucleotide analogs. The CPG and phosphoramidite reagents were purchased from Glen Research Corporation (Sterling, Va.). Following synthesis, the probes were deprotected and cleaved from the solid support matrix by treatment with concentrated ammonium hydroxide (30%) for two hours at 60° C. Next, the probes were purified using polyacrylamide gel electrophoresis followed by HPLC using standard procedures that will be familiar to those having an ordinary level of skill in the art.

The nucleic acid target used in the real-time amplification and detection procedures was purified rRNA of known concentration. Different target concentrations were tested in triplicate. Molecular beacons were used at a level of 0.2 pmol/μl (3 pmol/reaction). Reactions for amplifying GBS nucleic acids were conducted using from as low as 50 template copies/reaction up to as high as $5 \times 10^8$ template copies/reaction.

Reactions containing 3 pmol/reaction of T7 primer, 3 pmol/reaction of non-T7 primer, target polynucleotide, and 3 pmol/reaction molecular beacon in 15 μL of a buffered solution (final concentration: 50 mM Tris HC (pH 8.2 to 8.5), 35 mM KCl, 4 mM GTP, 4 mM ATP, 4 mM UTP, 4 mM CTP, 1 mM dATP, 1 mM dTTP, 1 mM dCTP, 1 mM dGTP, 20 mM $MgCl_2$, 20 mM N-Acetyl-L-Cysteine, and 5% (w/v) glycerol) were incubated in a dry heat block for 10 minutes at 60° C. to facilitate primer annealing. Following the 60° C. incubation step, reactions were transferred to a 42° C. heat block and then incubated for 2 minutes. Five microliter aliquots of an enzyme reagent that included both MMLV reverse transcriptase and T7 RNA polymerase enzymes were added to each of the reactions using a repeat pipettor. Tubes were vortexed briefly and then transferred to a Rotor-Gene 2000 (Corbett Research; Sydney, Australia) rotor that had been pre-warmed to 42° C. Amplification reactions were carried out at 42° C., fluorescence readings were taken every 30 seconds for 60 cycles, and the results analyzed in real-time using standard software that was bundled with the RG2000 instrument. Representative results from this procedure using different molecular beacons and different primer combinations are summarized in Tables 6 and 7, respectively.

TABLE 6

Measured Time-of-Emergence During Real-Time Detection Different Molecular Beacons

| Molecular Beacons | Time-of-Emergence with Different Primer Combinations (minutes) | | |
|---|---|---|---|
| | SEQ ID NOs: 4 & 11 | SEQ ID NOs: 4 & 12 | SEQ ID NOs: 4 & 13 |
| SEQ ID NO: 18 | 26.5 | 17.4 | ND |
| SEQ ID NO: 19 | 4.6 | 6.0 | 3.0 |

ND = Not Detected

The results presented in Table 6 confirmed that the amplification reactions containing 3 primer combinations, different GBS-specific molecular beacons and a fixed target concentration ($5 \times 10^8$ copies/rxn) desirably produced a fluorescent signal that increased with time until reaching a plateau except with primer combination SEQ ID NOs:4 & 13 and molecular beacon SEQ ID NO:18, Each of the molecular beacons used in the procedure included a fluorescein fluorophore at its 5'-end and a DABCYL quencher moiety at its 3'-end. All results were based on reactions that were included in triplicate.

TABLE 7

Measured Time-of-Emergence During Real-Time Detection Different Primer Combinations

| GBS Target (copies/rxn) | Time-of-Emergence Measured Using Molecular Beacon SEQ ID NO: 19 and Different Primer Combinations (minutes) | | | | | | | | |
|---|---|---|---|---|---|---|---|---|---|
| | SEQ ID Nos: 4 & 11 | SEQ ID NOs: 4 & 12 | SEQ ID NOs: 4 & 13 | SEQ ID NOs: 5 & 11 | SEQ ID NOs: 5 & 12 | SEQ ID NOs: 5 & 13 | SEQ ID NOs: 6 & 11 | SEQ ID NOs: 6 & 12 | SEQ ID NOs: 6 & 13 |
| $5 \times 10^8$ | NT | NT | 6.0 | NT | NT | NT | NT | NT | NT |
| $5 \times 10^7$ | NT | NT | 8.5 | NT | NT | NT | NT | NT | NT |
| $5 \times 10^6$ | 30.3 | 21.0 | 12.2 | NT | NT | NT | NT | NT | NT |
| $5 \times 10^5$ | ND | 26.6 | 15.7 | NT | NT | NT | NT | NT | NT |
| $5 \times 10^4$ | ND | 32.7 | 19.3 | NT | NT | NT | NT | NT | NT |
| $5 \times 10^3$ | ND | 39.8 | 23.8 | 48.9 | 32.1 | 23.6 | 35.7 | 39.7 | 22.9 |
| $5 \times 10^2$ | ND | 50.8 | 34.7 | 29.5 | 47.7‡ | 33.2 | 44.6 | 50.3 | 27.2 |
| $5 \times 10^1$ | ND | 55.6 | 44.1 | 47.0 | 53.6‡ | 49.3 | ND | 58.1‡ | 35.0 |

NT = Not Tested
ND = Not Detected
‡Only 2/3 replicates detected

The results shown in Table 7 confirmed that the amplification reactions containing different primer combinations and a fixed molecular beacon (SEQ ID NO:19) desirably produced a fluorescent signal that increased with time until reaching a plateau. All results were based on reactions that were included in triplicate. The results also showed that this particular molecular beacon was able to detect amplification product down to 50 copies/reaction. Only primer combinations SEQ ID NOs:5 & 12 and SEQ ID NOs:6 & 12 detected 2/3 replicates at the 50 copies/reaction level, while none of the 3 replicates were detected with primer combination SEQ ID NOs:6 & 11 at this level.

Each of the primer combinations tested gave at least some level of time-dependent analyte detection. The different primer combinations tested in the procedure behaved somewhat differently in the real-time assay format For example, reactions that included primer combinations SEQ ID NOs:4 & 13 and SEQ ID NOs:6 & 13 gave exceedingly rapid detection. The results presented in Table 7 further illustrate how the above-described primers and molecular beacons could be used in a highly sensitive assay for detecting GBS nucleic acids at very low levels of input template.

What is claimed:

1. A kit for amplifying and detecting a *Streptococcus agalactiae* target nucleic acid sequence, said kit comprising:
    a first primer, the base sequence of which consists of a 3' terminal target-complementary sequence and a first primer upstream sequence comprising a promoter sequence for an RNA polymerase, said 3' terminal target-complementary sequence of said first primer being contained within and comprising at least 25 contiguous bases of SEQ ID NO:2 or the full complement thereof, allowing for the presence of RNA base equivalents and nucleotide analogs;
    a second primer, the base sequence of which consists of a 3' terminal target-complementary sequence contained within and comprising at least 20 contiguous bases of SEQ ID NO:1 or the full complement thereof, allowing for the presence of RNA base equivalents and nucleotide analogs; and
    a probe, the base sequence of which consists of a target-complementary sequence and, optionally, one or more base sequences that are non-complementary to a nucleic acid containing said target nucleic acid sequence or its complement, said target-complementary sequence of said probe being contained within and comprising at least 16 contiguous bases of SEQ ID NO:3 or the full complement thereof, allowing for the presence of RNA base equivalents and nucleotide analogs.

2. The kit of claim 1, wherein said 3' terminal target-complementary sequence of said first primer is selected from the group consisting of SEQ ID NO:8, SEQ ID NO:9, SEQ ID NO:10, and the full complements thereof, allowing for the presence of RNA base equivalents and nucleotide analogs.

3. The kit of claim 2, wherein said 3' terminal target-complementary sequence of said second primer is selected from the group consisting of SEQ ID NO:4, SEQ ID NO:5, SEQ ID NO:6, and the full complements thereof, allowing for the presence of RNA base equivalents and nucleotide analogs.

4. The kit of claim 1, wherein said 3' terminal target-complementary sequence of said second primer is selected from the group consisting of SEQ ID NO:4, SEQ ID NO:5, SEQ ID NO:6, and the full complements thereof, allowing for the presence of RNA base equivalents and nucleotide analogs.

5. The kit of claim 1, wherein said target-complementary sequence of said probe is selected from the group consisting of SEQ ID NO:14, SEQ ID NO:15, SEQ ID NO:16, SEQ ID NO:17, and the full complements thereof, allowing for the presence of DNA base equivalents and nucleotide analogs.

6. The kit of claim 1, wherein said probe comprises said optional one or more base sequences that are non-complementary to a nucleic acid containing said target nucleic acid sequence or its complement.

7. The kit of claim 6, wherein said target-complementary sequence of said probe is selected from the group consisting of SEQ ID NO:14, SEQ ID NO:15, SEQ ID NO:16, SEQ ID NO:17, and the full complements thereof, allowing for the presence of DNA base equivalents and nucleotide analogs.

8. The kit of claim 6, wherein said probe further comprises a fluorophore moiety and a quencher moiety.

9. A kit for amplifying and detecting a *Streptococcus agalactiae* target nucleic acid sequence, said kit comprising:
    a first primer, the base sequence of which consists of a 3' terminal target-complementary sequence and a first primer upstream sequence comprising a promoter sequence for an RNA polymerase, said 3' terminal target-complementary sequence of said first primer being selected from the group consisting of SEQ ID NO:8, SEQ ID NO:9, SEQ ID NO:10, and the full complements thereof, allowing for the presence of RNA base equivalents and nucleotide analogs;
    a second primer, the base sequence of which consists of a 3' terminal target-complementary sequence selected from the group consisting of SEQ ID NO:4, SEQ ID NO:5, SEQ ID NO:6, and the full complements thereof, allowing for the presence of RNA base equivalents and nucleotide analogs; and
    a probe, the base sequence of which consists of a target-complementary sequence and, optionally, one or more base sequences that are non-complementary to a nucleic acid containing said target nucleic acid sequence or its complement, said target-complementary sequence of said probe being selected from the group consisting of SEQ ID NO:14, SEQ ID NO:15, SEQ ID NO:16, SEQ ID NO:17, and the full complements thereof, allowing for the presence of RNA base equivalents and nucleotide analogs.

10. The kit of claim 9, wherein said probe comprises said optional one or more base sequences that are non-complementary to a nucleic acid containing said target nucleic acid sequence or its complement.

11. The kit of claim 10, wherein said probe further comprises a fluorophore moiety and a quencher moiety.

12. The kit of claim 9, wherein:
    said 3' terminal target-complementary sequence of said first primer is SEQ ID NO:10 or the full complement thereof, allowing for the presence of RNA base equivalents and nucleotide analogs;
    said 3' terminal target-complementary sequence of said second primer is SEQ ID NO:4 or the full complement thereof, allowing for the presence of RNA base equivalents and nucleotide analogs; and
    said target-complementary sequence of said probe is SEQ ID NO:16 or the full complement thereof, allowing for the presence of RNA base equivalents and nucleotide analogs.

13. The kit of claim 12, wherein said probe comprises said optional one or more base sequences that are non-complementary to a nucleic acid containing said target nucleic acid sequence or its complement.

14. The kit of claim 13, wherein said probe further comprises a fluorophore moiety and a quencher moiety.

* * * * *

SEQUENCE LISTING

<160> NUMBER OF SEQ ID NOS: 22

<210> SEQ ID NO 1
<211> LENGTH: 37
<212> TYPE: DNA
<213> ORGANISM: Streptococcus agalactiae

<400> SEQUENCE: 1
aagtgtctgg tcaaacagtg aggtgtgata tgagtca                37

<210> SEQ ID NO 2
<211> LENGTH: 50
<212> TYPE: DNA
<213> ORGANISM: Streptococcus agalactiae

<400> SEQUENCE: 2
tgagcgagag aactctcgtt aaggaactcg gcaaaatggc cccgtaactt                50

<210> SEQ ID NO 3
<211> LENGTH: 20
<212> TYPE: DNA
<213> ORGANISM: Streptococcus agalactiae

<400> SEQUENCE: 3
gcgatacata tactctaccc                20

<210> SEQ ID NO 4
<211> LENGTH: 21
<212> TYPE: DNA
<213> ORGANISM: Streptococcus agalactiae

<400> SEQUENCE: 4
aagtgtctgg tcaaacagtg a                21

<210> SEQ ID NO 5
<211> LENGTH: 21
<212> TYPE: DNA
<213> ORGANISM: Streptococcus agalactiae

<400> SEQUENCE: 5
tggtcaaaca gtgaggtgtg a                21

<210> SEQ ID NO 6
<211> LENGTH: 20
<212> TYPE: DNA
<213> ORGANISM: Streptococcus agalactiae

<400> SEQUENCE: 6
gtgaggtgtg atatgagtca                20

```
<210> SEQ ID NO 7
<211> LENGTH: 27
<212> TYPE: DNA
<213> ORGANISM: Streptococcus agalactiae

<400> SEQUENCE: 7
aatttaatac gactcactat agggaga                                        27

<210> SEQ ID NO 8
<211> LENGTH: 25
<212> TYPE: DNA
<213> ORGANISM: Streptococcus agalactiae

<400> SEQUENCE: 8
tccttaacga gagttctctc gctca                                          25

<210> SEQ ID NO 9
<211> LENGTH: 29
<212> TYPE: DNA
<213> ORGANISM: Streptococcus agalactiae

<400> SEQUENCE: 9
gggccatttt gccgagttcc ttaacgaga                                      29

<210> SEQ ID NO 10
<211> LENGTH: 31
<212> TYPE: DNA
<213> ORGANISM: Streptococcus agalactiae

<400> SEQUENCE: 10
aagttacggg gccattttgc cgagttcctt a                                   31

<210> SEQ ID NO 11
<211> LENGTH: 52
<212> TYPE: DNA
<213> ORGANISM: Streptococcus agalactiae

<400> SEQUENCE: 11
aatttaatac gactcactat agggagatcc ttaacgagag ttctctcgct ca            52

<210> SEQ ID NO 12
<211> LENGTH: 56
<212> TYPE: DNA
<213> ORGANISM: Streptococcus agalactiae

<400> SEQUENCE: 12
aatttaatac gactcactat agggagaggg ccattttgcc gagttcctta acgaga        56

<210> SEQ ID NO 13
<211> LENGTH: 58
<212> TYPE: DNA
<213> ORGANISM: Streptococcus agalactiae

<400> SEQUENCE: 13
aatttaatac gactcactat agggagaaag ttacggggcc attttgccga gttcctta      58

<210> SEQ ID NO 14
<211> LENGTH: 16
<212> TYPE: RNA
<213> ORGANISM: Streptococcus agalactiae

<400> SEQUENCE: 14
uacauauacu cuaccc                                                    16
```

```
<210> SEQ ID NO 15
<211> LENGTH: 17
<212> TYPE: RNA
<213> ORGANISM: Streptococcus agalactiae

<400> SEQUENCE: 15
auacauauac ucuaccc                                                    17

<210> SEQ ID NO 16
<211> LENGTH: 18
<212> TYPE: RNA
<213> ORGANISM: Streptococcus agalactiae

<400> SEQUENCE: 16
gauacauaua cucuaccc                                                   18

<210> SEQ ID NO 17
<211> LENGTH: 20
<212> TYPE: RNA
<213> ORGANISM: Streptococcus agalactiae

<400> SEQUENCE: 17
gcgauacaua uacucuaccc                                                 20

<210> SEQ ID NO 18
<211> LENGTH: 26
<212> TYPE: RNA
<213> ORGANISM: Streptococcus agalactiae

<400> SEQUENCE: 18
ccgaguacau auacucuacc ccucgg                                          26

<210> SEQ ID NO 19
<211> LENGTH: 27
<212> TYPE: RNA
<213> ORGANISM: Streptococcus agalactiae

<400> SEQUENCE: 19
ccgagauaca uauacucuac cccucgg                                         27

<210> SEQ ID NO 20
<211> LENGTH: 28
<212> TYPE: RNA
<213> ORGANISM: Streptococcus agalactiae

<400> SEQUENCE: 20
ccgaggauac auauacucua ccccucgg                                        28

<210> SEQ ID NO 21
<211> LENGTH: 30
<212> TYPE: RNA
<213> ORGANISM: Streptococcus agalactiae

<400> SEQUENCE: 21
ccgaggcgau acauauacuc uaccccucgg                                      30

<210> SEQ ID NO 22
<211> LENGTH: 35
<212> TYPE: RNA
<213> ORGANISM: Streptococcus agalactiae

<400> SEQUENCE: 22
gcgguacggg uagaguauau guaucgcuag aagcu                                35
```